United States Patent [19]

Thieme et al.

[11] 4,237,278

[45] Dec. 2, 1980

[54] AMINO DERIVATIVES OF 2-METHYL-5-(2-HYDROXYSTYRYL)-1,3,4-THIADIAZOLE

[75] Inventors: Peter C. Thieme, Wachenheim; Fritz-Frieder Frickel, Ludwigshafen; Helmut Hagen, Frankenthal; Albrecht Franke, Wachenheim; Dieter Lenke, Ludwigshafen; Josef Gries, Wachenheim, all of Fed. Rep. of Germany

[73] Assignee: BASF Aktiengesellschaft, Fed. Rep. of Germany

[21] Appl. No.: 30,842

[22] Filed: Apr. 17, 1979

[30] Foreign Application Priority Data

Apr. 28, 1978 [DE] Fed. Rep. of Germany ....... 2818765

[51] Int. Cl.³ .................... A61K 31/425; C07D 23/00; C07D 23/14

[52] U.S. Cl. .................... 542/429; 424/270; 542/458

[58] Field of Search ................ 424/270; 542/429, 458

[56] References Cited

FOREIGN PATENT DOCUMENTS 2624918 12/1977 Fed. Rep. of Germany .
1307436 2/1973 United Kingdom .................... 424/263

Primary Examiner—Frederick E. Waddell
Attorney, Agent, or Firm—Keil & Witherspoon

[57] ABSTRACT

Novel alkylaminopropanol derivatives of 2-methyl-5-(2-hydroxystyryl)-1,3,4-thiadiazole and their addition salts with acids, their preparation, and pharmaceutical formulations, containing these compounds, which may be used for the treatment of coronary diseases of the heart, of hypertonia and of cardiac arrhythmias.

6 Claims, No Drawings

AMINO DERIVATIVES OF 2-METHYL-5-(2-HYDROXYSTYRYL)-1,3,4-THIADIAZOLE

The present invention relates to novel alkylaminopropanol derivatives of 2-methyl-5-(2-hydroxystyryl)-1,3,4-thiadiazole and their addition salts with acids, their preparation and pharmaceutical formulations, containing these compounds, which may be used for the treatment of coronary diseases of the heart, of hypertonia and of cardiac arrhythmias.

We have found that compounds of the general formula (I)

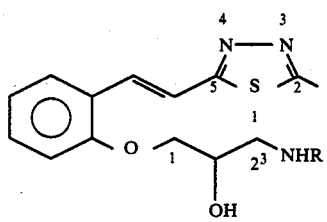

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl or cycloalkenyl with 3 to 8 carbon atoms in the ring, the cycloalkyl rings being unsubstituted or mono- or di-substituted by alkyl of 1 to 3 carbon atoms, and their addition salts with acids, exhibit valuable pharmacological properties.

Examples of straight-chain or branched alkyl of 1 to 8 carbon atoms are methyl, ethyl, propyl, isopropyl, n-butyl, isobutyl, sec.-butyl, tert.-butyl, pent-2-yl, 2-methyl-but-2-yl, 3-methyl-but-2-yl, 3-methyl-pent-3-yl, 2,3-dimethyl-but-2-yl, 3-ethyl-pent-3-yl, 2,4-dimethyl-pent-3-yl and 2,4,4-trimethyl-pentyl, and examples of substituted alkyl radicals are 1-methoxy-prop-2-yl, 2-hydroxyeth-1-yl, 1-hydroxy-but-2-yl, 3-hydroxy-3-methyl-but-1-yl and 1-cyclopropyl-eth-1-yl.

Amongst the alkyl radicals, those which are of 3 to 6 carbon atoms and are branched at the carbon in the α-position to the amino nitrogen are preferred. Accordingly, preferred alkyl radicals are isopropyl, tert.-butyl, 2-methyl-but-2-yl, sec.-butyl, 3-methyl-pent-3-yl and pent-2-yl. Possible substituents in the preferred alkyl radicals are, in particular, alkoxy of 1 to 3 carbon atoms, especially methoxy, an example of a preferred substituted alkyl therefore being 1-methoxy-prop-2-yl.

Examples of alkenyl or alkynyl of 2 to 8 carbon atoms are prop-1-en-3-yl, but-3-yn-2-yl, 2-methyl-but-3-yn-2-yl and 3-ethyl-pent-1-yn-3-yl. Amongst these, alkynyl radicals of 3 to 6 carbon atoms, eg. but-3-yn-2-yl and 2-methyl-but-3-yn-2-yl, are preferred.

Examples of cycloalkyl and cycloalkenyl are cyclopropyl, cyclobutyl, cyclopentyl, cycloheptyl and dimethylcyclohexyl, a particularly suitable alkyl substituent for the cyclic radicals mentioned being methyl. A preferred cyclic radical is cyclopropyl.

Accordingly, in addition to the compounds mentioned in the Examples, the following illustrate the compounds according to the invention, of the formula (I): 2-methyl-5-[2-(2-hydroxy-3-methylaminopropoxy)-styryl]-1,3,4-thiadiazole, 2-methyl-5-[2-(2-hydroxy-3-n-butylaminopropoxy)-styryl]-1,3,4-thiadiazole, 2-methyl-5-[2-(2-hydroxy-3-(2-methylbutyl-2-amino)-propoxy)-styryl]-1,3,4-thiadiazole, 2-methyl-5-[2-(2-hydroxy-3-(2,3-dimethyl-butyl-2-amino)-propoxy)-styryl]-1,3,4-thiadiazole, 2-methyl-5-[2-(2-hydroxy-3-(1-methylcyclobutylamino)-propoxy)-styryl]-1,3,4-thiadiazole, 2-methyl-5-[2-(2-hydroxy-3-cyclopentylamino-propoxy)-styryl]-1,3,4-thiadiazole, 2-methyl-5-[2-(2-hydroxy-3-cycloheptylamino-propoxy)-styryl]-1,3,4-thiadiazole, 2-methyl-5-[2-(2-hydroxy-3-(1-methoxypropyl-2-amino)-propoxy)-styryl]-1,3,4-thiadiazole, 2-methyl-5-[2-(2-hydroxy-3-(2-hydroxyethylamino)-propoxy)-styryl]-1,3,4-thiadiazole and 2-methyl-5-[2-(2-hydroxy-3-(prop-1-enyl-3-amino)-propoxy)-styryl]-1,3,4-thiadiazole.

The compounds according to the invention can be prepared by reacting a 2-methyl-5-styryl-1,3,4-thiadiazole of the general formula (II)

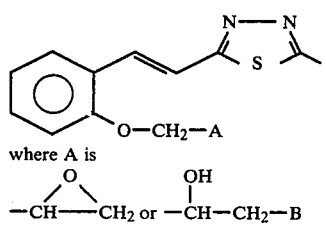

where A is

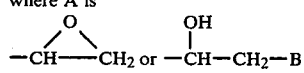

B being a nucleofugic leaving group, in the conventional manner with an amine of the general formula $H_2N-R$ where R has the above meanings, advantageously in a solvent and in the presence or absence of an acid-binding agent, and, if required, converting the resulting compound to the addition salt with a physiologically acceptable acid.

The leaving group B is preferably a halogen atom, especially chlorine, bromine or iodine. Further examples of suitable nucleofugic leaving groups are aromatic or aliphatic sulfonic acid radicals, e.g. the p-toluenesulfonic acid radical, p-bromobenzenesulfonic acid radical and the methanesulfonic acid radical.

The reactions are carried out at from 10° to 120° C., ie. at room temperature or elevated temperatures, advantageously at from 50° to 120° C. The reactions may be carried out under atmospheric pressure or in a closed vessel under superatmospheric pressure, where necessary with heating to the stated temperature range. In the case of volatile amines $H_2NR$, in particular, it can be advantageous to carry out the reaction in a closed system, ie. an autoclave.

The starting compounds can be reacted directly, ie. without addition of a diluent or solvent. Advantageously, however, the reactions are carried out in the presence of an inert diluent or solvent, for example a lower alcohol of 1 to 4 carbon atoms, eg. methanol, ethanol or propanol, isopropanol or ethanol being preferred, a lower saturated dialkyl ether, dialkyl glycol ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, dimethylsulfoxide or water, or a mixture of the said solvents.

An excess of the amine of the formula $H_2N$—R may also serve as a suitable diluent or solvent.

Preferred solvents for the reaction of 2-methyl-5-[2-(2,3-epoxypropoxy)-styryl]-1,3,4-thiadiazole with an amine R—$NH_2$ are lower alcohols, especially ethanol or isopropanol, the reaction preferably being carried out at from 50° C. to 100° C. and under atmospheric pressure.

For the nucleophilic replacement of a radical B, suitable solvents are lower aliphatic ketones, eg. acetone, methyl ethyl ketone or methyl isobutyl ketone, cyclic ethers, especially tetrahydrofuran or dioxane, or dialkylformamides, eg. dimethylformamide, preferred temperatures being from 90° to 120° C. If appropriate, the reaction is carried out in the presence of a catalytic amount of sodium iodide or potassium iodide.

The starting compound of the formula (II) may also be a mixture of the epoxide with a halohydrin, since the industrial manufacture of the starting compounds of the formula II under certain circumstances gives such mixtures.

In an advantageous embodiment of the nucelophilic replacement of the radical B by the amine used, the reaction is carried out in the presence of a base as the acid-binding agent. Preferred bases are alkali metal hydroxides, carbonates, bicarbonates or alcoholates or a tertiary organic amine, such as pyridine or a trialkylamine, eg. trimethylamine or triethylamine. Amongst the alkali metal compounds, those of sodium and potassium are preferred. The base is used in stoichiometric amount or in slight excess. It is under certain circumstances advantageous to use an excess of the amine $H_2N$—R, employed for the reaction, so as to serve simultaneously as the acid-binding agent.

The time required to complete the reaction depends on the reaction temperature and is in general from 2 to 15 hours. The reaction product can be isolated in the conventional manner, for example by filtration, or by distilling the diluent or solvent off the reaction mixture. The compound obtained is purified in the conventional manner, for example by recrystallization from a solvent, by conversion to an addition compound with an acid, or by column chromatography.

The starting compounds of the formula (II) can be obtained by alkylating 2-methyl-5-(2-hydroxystyryl)-1,3,4-thiadiazole (which can be prepared by condensing salicylaldehyde with 2,5-dimethyl-1,3,4-thiadiazole, as described in Example I, compound 1) with an epihalohydrin or an α,ω-dihalo-2-propanol. Suitable epihalohydrins are epichlorohydrin, epibromohydrin and epiiodohydrin and suitable α,ω-dihalo-2-propanols are in particular 1,3-dichloro-2-propanol and 1,3-dibromo-2-propanol.

The reactions of 2-methyl-5-(2-hydroxystyryl)-1,3,4-thiadiazole, to give the starting compounds of the formula (II), are advantageously carried out at from 0° to 120° C. under atmospheric pressure, or in a closed vessel under superatmospheric pressure. The reactions are advantageously carried out in an inert diluent or solvent, for example a lower aliphatic ketone, eg. acetone, methyl ethyl ketone or methyl isobutyl ketone, a lower alcohol of 1 to 4 carbon atoms, e.g. methanol, ethanol, propanol or butanol, an aliphatic or cycloaliphatic ether, eg. a dialkyl ether, tetrahydrofuran or dioxane, a dialkylformamide, eg. dimethylformamide or diethylformamide, or dimethylsulfoxide or hexamethylphosphorotriamide, or using excess alkylating agent as the diluent or solvent.

The reactions are preferably carried out in the presence of a base as the acid-binding agent. Suitable bases are alkali metal carbonates, bicarbonates, hydroxides, hydrides or alcoholates, especially of sodium or potassium, basic oxides, eg. aluminum oxide or calcium oxide, or organic tertiary bases, eg. pyridine, piperidine or lower trialkylamines, eg. trimethylamine or triethylamine. The base may be used in a catalytic amount relative to the alkylating agent employed, or in the stoichiometric amount or in slight excess.

Preferably, 2-methyl-5-(2-hydroxystyryl)-1,3,4-thiadiazole is reacted with epibromohydrin or 1,2-dibromopropan-2-ol in a solvent mixture of an ether and a polar aprotic solvent, especially tetrahydrofuran and hexamethylphosphorotriamide, at from 0° to 50° C.

According to a further method of preparation, the compounds of the general formula (I) are prepared by alkylating 2-methyl-5-(2-hydroxystyryl)-1,3,4-thiadiazole with a compound of the general formula (III) or (IV)

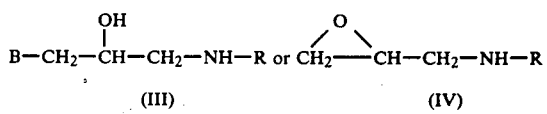

where B and R have the above meanings, including the preferred meanings, advantageously in a solvent, and in the presence or absence of an acid-binding agent, at from 40° to 120° C., in the conventional manner, and the resulting compounds are converted to the addition salts with physiologically acceptable acids. This reaction can for example be carried out under the conditions described in Swiss Pat. No. 451,115 or in German laid-open application DOS No. 2,007,751.

The alkylation of 2-methyl-5-(2-hydroxystyryl)-1,3,4-thiadiazole with a compound of the formula (III) is preferably carried out in the presence of an acid-binding agent, such as an alkali metal hydroxide, carbonate, bicarbonate or alcoholate, or of a tertiary organic amine, preferably pyridine or a tertiary aliphatic amine, eg. trimethylamine or triethylamine. Amongst the alkali metal compounds, those of sodium and potassium are preferred. The base is advantageously used in the stoichiometric amount or in slight excess. It is also possible, for example, to use the starting compound in the form of its alkali metal salt, eg. the sodium salt or potassium salt.

The alkylation reactions are advantageously carried out in an inert diluent or solvent, for example a lower aliphatic alcohol of 1 to 4 carbon atoms, eg. methanol, ethanol, propanol, isopropanol or a butanol, or a lower aliphatic ketone, eg. acetone, methyl ethyl ketone or methyl isobutyl ketone, a cyclic ether, eg. tetrahydrofuran or dioxane, a dialkylformamide, eg. dimethylformamide or diethylformamide, or dimethylsulfoxide or hexamethylphosphorotriamide, or a mixture of the said solvents. Advantageously, the reaction is accelerated, or terminated, by heating, for example at 40°-120° C., preferably 80°-100° C. Amongst the solvents, the lower aliphatic ketones, dialkylformamides and dimethylsulfoxide are preferred.

Because of the presence of the carbon-carbon double bond, the novel compounds of the formula (I) can be in the form of cis-trans-isomer mixtures. As a rule, however, the trans-isomers are obtained after the conventional physical purification processes, such as fractional crystallization, chromatography or sublimation.

The novel compounds of the formula (I) possess a chirality center on carbon atom 2 of the aliphatic side chain and are obtained as racemates which can be separated into the optically active antipodes by conventional methods, for example by forming diastereomeric salts with optically active auxiliary acids, such as dibenzoyltartaric acid, camphor-10-sulfonic acid, ditoluyltartaric acid or 3-bromocamphor-8-sulfonic acid.

If required, the novel compounds obtained are converted to addition salts with physiologically acceptable acids. Examples of conventional physiologically acceptable inorganic and organic acids are, respectively, hydrochloric acid, hydrobromic acid, phosphoric acid and sulfuric acid, and oxalic acid, maleic acid, fumaric acid, lactic acid, tartaric acid, malic acid, citric acid, salicylic acid, adipic acid and benzoic acid; suitable acids may also be found in Fortschritte der Arzneimittelforschung, 10 (1966), 224–225, Birkhäuser Verlag, Basel and Stuttgart, and in Journal of Pharmaceutical Sciences, 66 (1977), 1–5.

The addition salts with acids are as a rule obtained in the conventional manner by mixing the free base, or a solution thereof, with the appropriate acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. Mixtures of the said solvents can also be used, to produce better crystallization. In addition, pharmaceutically acceptable aqueous solutions of addition compounds of the aminopropanol derivatives of the general formula (I) with acids can also be prepared by dissolving the free base of the general formula (I) in an aqueous solution of the acid.

The compounds according to the invention and their addition salts with physiologically acceptable acids exhibit valuable pharmacological properties.

They may be used as drugs having a beta-sympatholytic action, for the treatment of coronary diseases of the heart, or of hypertonia and of cardiac arrhythmias.

The beta-sympatholytic action was tested on cats, in comparison with the known beta-sympatholytic agent propranolol. The following test methods were used:

1. Beta-sympatholytic action

Isoproterenol (1 μg/kg, given intravenously) in narcotized cats (weight 2–4 kg) causes increases in pulse rate of, on average, 40%. Beta-sympatholytic agents inhibit such tachycardia. Isoproterenol was administered before, and 10 minutes and 40 minutes after, the intravenous administration of the test substances. Linear relationships are found between the logarithms of the administered doses (mg/kg) of the test substances and the inhibition of isoproterenol-induced tachycardia (%). From these relationships, the ED 50%, ie. the doses which inhibit the isopropterenol-induced tachycardia by 50% are determined.

2. Acute toxicity

To determine the mean lethal dose (LD 50), the substances were administered intraperitoneally to female NMRI mice (weight 19–26 g).

The results summarized in the Table show that the substances according to the invention are distinguished by an unusually high beta-sympatholytic activity. The cardiac beta-1-receptors, which are significant as far as pharmacotherapeutic use is concerned, are blocked at doses which are lower by a factor of 12 (Example 2) to 25 (Example 3) than those of the comparison substance propranolol. It follows from this high activity and from the lethal doses, which are of the same order of magnitude as the lethal dose of propranolol, that the therapeutic range is increased, compared to propranolol, by a factor of from 7.6 (Example 2) to 30.7 (Example 7).

TABLE

Beta-sympatholytic action and acute toxicity

| Substance | Beta sympatholytic action[1] ED 50%[2] | R.A.[3] | Acute toxicity LD 50[4] | Therapeutic range[5] absolute | relative[6] |
|---|---|---|---|---|---|
| Propranolol | 0.141 | 1.00 | 108 | 766 | 1.00 |
| Compound from Example 1 | 0.010 | 14.10 | 83.0 | 8,300 | 10.84 |
| Compound from Example 2 | 0.012 | 11.75 | 69.4 | 5,780 | 7.55 |
| Compound from Example 3 | 0.00559 | 25.22 | 58.8 | 10,520 | 13.73 |
| Compound from Example 7 | 0.0111 | 12.70 | 261 | 23,500 | 30.68 |

[1] Inhibition of isoproterenol-induced tachycardia in cats under hexobarbital narcosis. Intravenous administration.
[2] Dose (mg/kg) which inhibits the isoproterenol-induced tachycardia by 50%.
[3] Relative activity. Propranolol = 1.00.
[4] Mice. Intraperitoneal administration.
[5] $\frac{LD\ 50}{ED\ 50\%}$
[6] Propranolol = 1.00.

Accordingly, the present invention also relates to therapeutic agents or formulations which in addition to conventional excipients and diluents contain a compound of the formula (I) as the active ingredient, and to the use of the novel compounds for therapeutic purposes.

The therapeutic agents or formulations are prepared in the conventional manner with the conventional excipients or diluents and the conventional pharmaceutical auxiliaries, in accordance with the desired route of administration, and so as to provide a suitable dose.

The preferred formulations are those suitable for oral administration. Examples of these are tablets, film tablets, dragees, capsules, pills, powders, solutions or suspensions, or forms which exert a depot effect.

Of course, formulations for parenteral administration; eg. injection solutions, are also suitable. Suppositories are a further example of suitable formulations.

Appropriate tablets can be obtained, for example, by mixing the active ingredient with conventional auxiliaries, for example inert excipients, eg. dextrose, sugar, sorbitol, mannitol, polyvinylpyrrolidone, calcium carbonate, calcium phosphate or lactose, disintegrating agents, eg. corn starch or alginic acid, binders, eg. starch or gelatin, lubricants, eg. magnesium stearate or talc, and/or agents added in order to achieve a depot effect, eg. carboxypolymethylene, carboxymethylcellulose, cellulose acetate-phthalate or polyvinyl acetate. The tablets can also consist of several layers.

Dragees may be produced by coating cores, prepared similarly to the tablets, with agents conventionally used in dragee coatings, for example collidone or shellac, gum arabic, talc, titanium dioxide or sugar. The dragee coating can also consist of several layers, and the auxiliaries mentioned above in connection with tablets can be used. Solutions or suspensions containing the active ingredients according to the invention may in addition contain flavor improvers, eg. saccharin, cyclamate or sugar, and also, for example, flavorings such as vanillin or orange extract. Furthermore, they may contain suspending assistants, such as sodium carboxymethylcellulose, or preservatives, such as p-hydroxybenzoates. Capsules containing the active ingredient can be prepared, for example, by mixing the active ingredient with an inert excipient, such as lactose or sorbitol, and encapsulating the mixture in gelatin capsules.

Suitable suppositories can be prepared, for example, by mixing the active ingredient with suitable excipients, eg. neutral fats, polyethylene glycol or derivatives of these.

For man, a suitable single dose of the compounds according to the invention is from 1 to 100 mg, preferably from 2 to 50 mg.

Some compounds which warrant special mention because of their activity are 2-methyl-5-[2-(2-hydroxy-3-isopropylamino-propoxy)-styryl]-1,3,4-thiadiazole, 2-methyl-5-[2-(2-hydroxy-3-cyclopropylamino-propoxy)-styryl]-1,3,4-thiadiazole, 2-methyl-5-[2-(2-hydroxy-3-tert.-butylamino-propoxy)-styryl]-1,3,4-thiadiazole and 2-methyl-5-[2-(2-hydroxy-3-(but-1-ynyl-3-amino)-propoxy)-styryl]-1,3,4-thiadiazole.

The Examples which follow illustrate the invention.

I. PREPARATION OF STARTING COMPOUNDS

Compound 1:
2-Methyl-5-(2-hydroxy-styryl)-1,3,4-thiadiazole 570 g (5 moles) of 2,5-dimethyl-1,3,4-thiadiazole and 275 g (2.5 moles) of salicylaldehyde are mixed and the mixture is slowly heated to 150° C. whilst passing nitrogen through it. The mixture is kept at 150° C. for 30 hours and is then cooled, the excess 2,5-dimethyl-1,3,4-thiadiazole is distilled off and the residue is recrystallized from methylglycol. 304 g (56% of theory) of yellow crystals of melting point 253°–254° are obtained.

$C_{11}H_{10}N_2OS$ (218): calculated: C, 60.6; H, 4.6; N, 12.8. found: C, 59.8; H, 4.6; N, 12.4.

Compound 2:
2-Methyl-5-[2-(2,3-epoxypropoxy)-styryl]-1,3,4-thiadiazole 3.72 g (0.085 mole) of 55% strength sodium hydride in paraffin oil are suspended in 150 ml of absolute tetrahydrofuran and 18.6 g (0.085 mole) of 2-(2-hydroxystyryl)-5-methyl-1,3,4-thiadiazole in 200 ml of absolute hexamethylphosphorotriamide are then added dropwise at 0°–3° C. in the course of 1.5 hours. Stirring is continued at room temperature for 1 hour, after which 11.7 g (0.085 mole) of dibromohydrin are added dropwise. The solution is left to stand at room temperature for 16 hours and is then poured onto 1.5 liters of ice water and 0.5 liter of saturated sodium chloride solution. The solid obtained is filtered off and recrystallized from acetone. 11.8 g (51% of theory) of yellow crystals are obtained. Melting point 134°–135° C.

$C_{14}H_{14}N_2O_2S$ (274): calculated: C, 61.3; H, 5.1; O, 11.7; S, 11.7; N, 10.2. found: C, 61.3; H, 5.4; O, 13.5; S, 10.5; N, 8.4.

Compound 3:
2-Methyl-5-[2-(2-hydroxy-3-chloro-propoxy)-styryl]-1,3,4-thiadiazle 1 g of 2-methyl-5-[2-(2,3-epoxypropoxy)-styryl]-1,34-thiadiazole is left to stand for 12 hours in a mixture of 100 ml of ethanol and 5 ml of a 3 N solution of hydrogen chloride in ether. The precipitate formed is filtered off, washed neutral with ether and chromatographed on silica gel, using chloroform. The product eluates, when evaporated to dryness, give spectroscopically pure 2-methyl-5-[2-(2-hydroxy-3-chloro-propoxy)-styryl]-1,3,4-thiadiazole of melting point 168°–170° C.

1H-NMR spectrum (CDCl$_3$, TMS as internal standard) = 2.5–3.3 (m, 6H), 4.8 (s, 1H), 5.5–6.0 (m, 3H and OH), 6.1–6.3 (m, 2H), 7.3 (s, 3H)

II. PREPARATION OF COMPOUNDS ACCORDING TO THE INVENTION

EXAMPLE 1

2-Methyl-5-[2-(2-hydroxy-3-isopropylamino-propoxy)-styryl]-1,3,4-thiadiazole 7 g (0.025 mole) of 2-methyl-5-[2-(2,3-epoxy-propoxy)-styryl]-1,3,4-thiadiazole and 2.9 g (0.05 mole) of isopropylamine are brought together in 100 ml of isopropanol and the mixture is refluxed for 7 hours. After cooling, the solvent is distilled off and the residue obtained is recrystallized from toluene.

5.1 g (61% of theory), melting point 156°–157°.
$C_{17}H_{23}O_2N_3S$ (333): calculated: C, 61.2; H, 7.0; N, 12.6. found: C, 60.8; H, 6.8; N, 12.1.

EXAMPLE 2

2-Methyl-5-[2-(2-hydroxy-3-cyclopropylamino-propoxy)-styryl]-1,3,4-thiadiazole 3.8 g (0.014 mole) of 2-methyl-5-[2-(2,3-epoxypropoxy)-styryl]-1,3,4-thiadiazole and 1.0 g (0.018 mole) of cyclopropylamine are reacted by the method described in Example 1. 2.2 g (48% of theory) of yellow crystals are obtained from toluene; melting point 144°–145° C.

$C_{17}H_{21}N_3O_2S$ (331): calculated: C, 61.6; H, 6.4; N, 12.7. found: C, 60.8; H, 6.1; N, 12.3.

EXAMPLE 3

2-Methyl-5-[2-(2-hydroxy-3-tert.-butylamino-propoxy)-styryl]-1,3,4-thiadiazole 7 g (0.025 mole) of 2-methyl-5-[2-(2,3-epoxy-propoxy)-styryl]-1,3,4-thiadiazole and 2.1 g (0.028 mole) of tert.-butylamine are reacted by the method described in Example 1. 3.8 g (44% of theory) of yellow crystals are obtained from toluene; melting point 110°–112° C.

$C_{18}H_{25}N_3O_2S$: calculated: C, 62.2; H, 7.2; N, 12.1. found: C, 62.3; H, 7.3; N, 11.6.

EXAMPLE 4

2-Methyl-5-[2-(2-hydroxy-3-(butyl-2-amino)-propoxy)-styryl]1,3,4-thiadiazole 6 g (0.022 mole) of 2-methyl-5-[2-(2,3-epoxypropoxy)-styryl]-1,3,4-thiadiazole and 1.6 g (0.022 mole) of 2-butylamine, reacted by the method described in Example 1, give 3.5 g (45% of theory) of yellow crystals. Melting point 135°–136° C.

$C_{18}H_{25}N_3O_2S$ (347): calculated: C, 62.2; H, 7.2; N, 12.1. found: C, 62.5; H, 7.1; N, 11.7.

EXAMPLE 5

2-Methyl-5-[2-(2-hydroxy-3-(pentyl-2-amino)-propoxy)-styryl]-1,3,4-thiadiazole 6 g (0.022 mole) of 2-methyl-5-[2-(2,3-epoxypropoxy)-styryl]-1,3,4-thiadiazole and 1.9 g (0.022 mole) of 2-amino-pentane are reacted by the method described in Example 1. 2.6 g (33% of theory) of yellow crystals are obtained. Melting point 112°–113° C.

$C_{19}H_{27}N_3O_2S$ (362): calculated: C, 61.3; H, 7.5; N, 11.6. found: C, 63.3; H, 7.2; N, 11.7.

EXAMPLE 6

2-Methyl-5-[2-(2-hydroxy-3-(1-cyclopropyl-ethyl-1-amino)-propoxy)-styryl]-1,3,4-thiadiazole 6 g (0.022 mole) of 2-methyl-5-[2-(2,3-epoxypropoxy)-styryl]-1,3,4-thiadiazole and 2.2 g (0.022 mole) of 1-cyclopropyl-1-amino-ethane in 100 ml of isopropanol are refluxed for 30 hours. The reaction mixture is then concentrated on a rotary evaporator and the product is freed from impurities on a 45×5 cm column of Silica gel 60 (0.063–0.200 mm) from Merck. The eluent is a 4:1 mixture of chloroform and methanol. The purity of the fractions is examined by thin layer chromatography. 2.6 g (33% of theory) of yellow crystals are obtained. Melting point 114°–116° C.

$C_{19}H_{25}N_3O_2S$ (359): calculated: C, 63.5; H, 7.0; N, 11.7. found: C, 62.6; H, 6.8; N, 11.4.

EXAMPLE 7

2-Methyl-5-[2-(2-hydroxy-3-(but-1-ynyl-3-amino)-propoxy)-styryl]-1,3,4-thiadiazole 6 g (0.022 mole) of 2-methyl-5-[2-(2,3-epoxy-propoxy)styryl]-1,3,4-thiadiazole and 1.5 g (0.022 mole) of but-1-yn-yl-3-amine are reacted by the method described in Example 1. The reaction solution is freed from insoluble residue by filtration and is concentrated on a rotary evaporator. 6.2 g of an oil remain, and are purified chromatographically on Silica gel 60 (0.062–0.200 mm) from merck, using a 4:1 mixture of chloroform and methanol as the eluant. The purified oil can be caused to crystallize by means of isopropanol/ether. 2.1 g (28% of theory). Melting point 143°–145° C.

$C_{18}H_{21}N_3O_2S$ (343): calculated: C, 62.9; H, 6.2; N, 12.1. found: C, 61.6; H, 6.2; N, 12.3.

EXAMPLE 8

2-Methyl-5-[2-(2-hydroxy-3-(3-methyl-but-1-ynyl-3-amino)-propoxy)-sturyl]-1,3,4-thiadiazole 6 g (0.022 mole) of 2-methyl-5-[2-(2,3-epoxypropoxy)-styryl]-1,3,4-thiadiazole and 1.8 g (0.022 mole) of 3-methyl-3-amino-but-1-yne are reacted by the method described in Example 7. 5.8 g of a yellow oil are obtained, and are dissolved in 100 ml of isopropanol. A solution of hydrogen chloride in ether is added until the mixture reacts acid, after which 100 ml of ether are introduced. The precipitate is filtered off, washed with ether and dried. 4.3 g (42% of theory), melting point 132°–133° C.

$C_{19}H_{23}N_3O_2S.2HCl.2H_2O$ (466): calculated: C, 50.8; H, 6.0; N, 9.3; Cl, 15.8. found: C, 50.0; H, 5.8; N, 8.5; Cl, 14.4.

EXAMPLE 9

2-Methyl-5-[2-(2-hydroxy-3-(3-ethyl-pent-1-ynyl-3-amino)-propoxy)-styryl]-1,3,4-thiadiazole 7 g (0.025 mole) of 2-methyl-5-[2-(2,3-epoxypropoxy)-styryl]-1,3,4-thiadiazole and 2.8 g (0.025 mole) of 3-ethyl-3-amino-pent-1-yne are reacted by the method described in Example 8, and give 3.7 g (32% of theory) of the hydrochloride of melting point 157°–159° C.

$C_{21}H_{27}N_3O_2S.1.5HCl.1.5H_2O$ (467): calculated: C, 53.9; H, 6.7; N, 8.9; Cl, 11.5. found: C, 53.4; H, 6.5; N, 8.9; Cl, 11.8.

EXAMPLE 10

2-Methyl-5-[2-(2-hydroxy-3-tert.-butylamino-propoxy)-styryl]-1,3,4-thiadiazole 1.6 g of 2-methyl-5-[2-(2-hydroxy-3-chloro-propoxy)-styryl]-1,3,4-thiadiazole and 10 ml of tert.-butylamine in 50 ml of dioxane are heated for 10 hours at 100° C. in an autoclave. After distilling off the volatile constitutents under reduced pressure the highly viscous crude product is chromatographed over a dry silica gel column, using chloroform. The residue obtained on evaporating the eluates containing the product gives 2-methyl-5-[2-(2-hydroxy-3-tert.-butylamino-propoxy)styryl]-1,3,4-thiadiazole. The compound, in its isolated form, is identical with the compound obtained as described in Example 3.

The compounds of Examples 1, 2 and 4 to 9 are also obtained in the same manner if 2-methyl-5-[2-(2-hydroxy-3-chloro-propoxy)-styryl]-1,3,4-thiadiazole is reacted with the corresponding amine. Formulation Examples prepared in the conventional manner:

| 1. Tablets: | |
|---|---|
| (a) An active ingredient of the formula I | 5mg |
| Lactose | 200 mg |
| Methylcellulose | 15 mg |
| Corn starch | 50 mg |
| Talc | 11 mg |
| Magnesium stearate | 4 mg |
| | 285 mg |
| (b) An active ingredient of the formula I | 20 mg |
| Lactose | 178 mg |
| Avicel | 80 mg |
| Polywachs 6000 | 20 mg |
| Magnesium stearate | 2 mg |
| | 300 mg |
| (c) An active ingredient of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 280 mg |

The active ingredient is moistened with a 10% strength aqueous solution of the polyvinylpyrrolidone, forced through a sieve of 1.0 mm mesh width and dried at 50° C. The granules thus obtained are mixed with polyethylene glycol (mean molecular weight 4,000), hydroxypropylmethylcellulose, talc and magnesium stearate and the mixture is pressed to give tablets each weighing 280 mg.

| 2. Example of dragees: | |
|---|---|
| An active ingredient of the formula I | 60 mg |

| -continued | |
|---|---|
| Lactose | 90 mg |
| Corn starch | 60 mg |
| Polyvinylpyrrolidone | 6 mg |
| Magnesium stearate | 1 mg |
| | 217 mg |

The mixture of the active ingredient, lactose and corn starch is granulated by moistening with an 8% strength aqueous solution of the polyvinylpyrrolidone and forcing through a 1.5 mm sieve, and the granules are dried at 50° C. and then forced through a 1.0 mm sieve. The granules resulting from the last operation are mixed with magnesium stearate and molded into dragee cores. These cores are coated in the conventional manner with a shell consisting essentially of sugar and talc.

| 3. Capsule formulation: | |
|---|---|
| An active ingredient of the formula I | 5.0 mg |
| Magnesium stearate | 2.0 mg |
| Lactose | 19.3 mg |
| 4. Injection solution: | |
| An active ingredient of the formula I | 10 mg |
| Sodium chloride | 9 mg |
| Distilled water to make up to 1.0 ml | |

We claim:

1. A compound of the general formula (I)

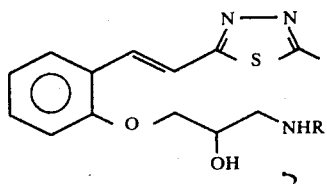

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl or cycloalkenyl with 3 to 8 carbon atoms in the ring, the cycloalkyl rings being unsubstituted or mono- or di-substituted by alkyl of 1 to 3 carbon atoms, and its addition salts with acids.

2. A compound of the formula I as claimed in claim 1, where R is alkyl of 3 to 6 carbon atoms which is branched at the carbon in the α-position to the nitrogen, and which is unsubstituted or substituted by alkoxy of 1 to 3 carbon atoms or where R is alkenyl or alkynyl of 2 to 8 carbon atoms, or is cyclopropyl.

3. 2-Methyl-5-[2-(2-hydroxy-3-isopropylamino-propoxy)-styryl]-1,3,4-thiadiazole.

4. 2-Methyl-5-[2-(2-hydroxy-3-cyclopropylamino-propoxy)-styryl]-1,3,4-thiadiazole.

5. 2-Methyl-5-[2-(2-hydroxy-3-tert.-butylamino-propoxy)-styryl]-1,3,4-thiadiazole.

6. 2-Methyl-5-[2-(2-hydroxy-3-(but-1-ynyl-3-amino)-propoxy)-styryl]-1,3,4-thiadiazole.

* * * * *